(12) United States Patent
Flitsch et al.

(10) Patent No.: US 9,615,917 B2
(45) Date of Patent: Apr. 11, 2017

(54) ENERGIZED OPHTHALMIC LENS

(71) Applicant: Johnson & Johnson Vision Care, Inc., Jacksonville, FL (US)

(72) Inventors: Frederick A. Flitsch, New Windsor, NY (US); Daniel B. Otts, Fruit Cove, FL (US); Randall B. Pugh, St. Johns, FL (US)

(73) Assignee: Johnson & Johnson Vision Care, Inc., Jacksonville, FL (US)

( * ) Notice: Subject to any disclaimer, the term of this patent is extended or adjusted under 35 U.S.C. 154(b) by 0 days.

(21) Appl. No.: 14/796,358

(22) Filed: Jul. 10, 2015

(65) Prior Publication Data

US 2015/0378176 A1   Dec. 31, 2015

Related U.S. Application Data

(63) Continuation of application No. 13/358,753, filed on Jan. 26, 2012, which is a continuation-in-part of (Continued)

(51) Int. Cl.
*A61F 2/16* (2006.01)
*H01L 23/58* (2006.01)
(Continued)

(52) U.S. Cl.
CPC ............. *A61F 2/1624* (2013.01); *A61F 2/16* (2013.01); *A61F 2/1648* (2013.01); *H01L 23/58* (2013.01); *A61F 2/1659* (2013.01); *A61F 2210/0057* (2013.01); *A61F 2250/0001* (2013.01); *G02C 7/04* (2013.01); *G02C 7/049* (2013.01); *G02C 7/083* (2013.01); *H01L 23/64* (2013.01); *H01L 25/0657* (2013.01); *H01L 25/16* (2013.01); *H01L 25/18* (2013.01); (Continued)

(58) Field of Classification Search
CPC .... A61F 2/1613; A61F 2/1624–2/1637; A61F 2/1648; A61F 2002/164; A61F 2002/1643; A61F 2002/1645; A61F 2002/1697; A61F 2210/0076
See application file for complete search history.

(56) References Cited

U.S. PATENT DOCUMENTS 4,268,132 A   5/1981   Neefe
5,219,497 A   6/1993   Blum
(Continued)

FOREIGN PATENT DOCUMENTS

CN   102159381 A   8/2011
CN   102196789 A   9/2011
(Continued)

OTHER PUBLICATIONS

Pandey et al., "A Fully Integrated RF-Powered Contact Lens with a Single Element Display", Dec. 2010, IEEE Transaction on Biomedical Circuits and Systems, vol. 4, No. 6, pp. 454-461.

*Primary Examiner* — Howie Matthews

(57) ABSTRACT

This invention discloses methods and apparatus for providing an ophthalmic lens with a stacked integrated component device for function. In some embodiments, the stacked integrated component device may contain an energy source capable of powering an electrical component incorporated into the lens.

4 Claims, 10 Drawing Sheets

Related U.S. Application Data application No. 12/557,016, filed on Sep. 10, 2009, now abandoned.

(60) Provisional application No. 61/192,765, filed on Sep. 22, 2008.

(51) Int. Cl.

| | | |
|---|---|---|
| G02C 7/04 | (2006.01) | |
| G02C 7/08 | (2006.01) | |
| H01L 23/64 | (2006.01) | |
| H01L 25/065 | (2006.01) | |
| H01L 25/16 | (2006.01) | |
| H01L 25/18 | (2006.01) | |

(52) U.S. Cl.
CPC ........... *H01L 2223/6677* (2013.01); *H01L 2224/16225* (2013.01); *H01L 2224/48091* (2013.01); *H01L 2924/19105* (2013.01)

(56) References Cited

U.S. PATENT DOCUMENTS

| | | | |
|---|---|---|---|
| 5,682,210 | A | 10/1997 | Weirich |
| 6,217,171 | B1 | 4/2001 | Auten |
| 6,364,482 | B1 | 4/2002 | Roffman |
| 6,638,304 | B2 | 10/2003 | Azar |
| 7,794,643 | B2 | 9/2010 | Watanabe |
| 2004/0027536 | A1 | 2/2004 | Blum |
| 2004/0084790 | A1 | 5/2004 | Blum |
| 2005/0099594 | A1 | 5/2005 | Blum |
| 2006/0181676 | A1 | 8/2006 | Tucker |
| 2007/0231575 | A1 | 10/2007 | Watanabe |
| 2008/0002149 | A1 | 1/2008 | Fritsch |
| 2008/0208335 | A1 | 8/2008 | Blum |
| 2009/0033863 | A1 | 2/2009 | Blum |
| 2009/0105817 | A1 * | 4/2009 | Bretthauer ............ A61B 3/113 623/4.1 |
| 2010/0072643 | A1 | 3/2010 | Pugh |
| 2010/0079724 | A1 | 4/2010 | Pugh |

FOREIGN PATENT DOCUMENTS

| | | |
|---|---|---|
| CN | 102727218 A | 10/2012 |
| EP | 1342560 A2 | 9/2003 |
| EP | 1736291 A2 | 12/2006 |
| EP | 1747879 A2 | 1/2007 |
| EP | 1760515 A2 | 3/2007 |
| EP | 1849574 A2 | 10/2007 |
| EP | 1849589 A2 | 10/2007 |
| EP | 1262307 B1 | 2/2010 |
| JP | 1286809 A | 11/1989 |
| JP | 2005535942 A | 11/2005 |
| TW | 200532278 A | 10/2005 |
| WO | WO2007050402 A2 | 5/2007 |
| WO | WO2008109867 A2 | 9/2008 |
| WO | WO2009105261 A1 | 8/2009 |
| WO | WO2010051225 A1 | 5/2010 |

* cited by examiner

ENERGIZED OPHTHALMIC LENS

CROSS REFERENCE TO RELATED PATENT APPLICATIONS

This application is a continuation of U.S. application Ser. No. 13/358,753, filed Jan. 26, 2012, which is a continuation-in-part of U.S. application Ser. No. 12/557,016, filed Sep. 10, 2009, which claims the benefit of U.S. Provisional Application No. 61/192,765, filed Sep. 22, 2008.

FIELD OF USE

This invention describes an energized biomedical device and, more specifically, in some embodiments, an energized ophthalmic lens.

BACKGROUND OF THE INVENTION

Traditionally an ophthalmic device, such as a contact lens, an intraocular lens or a punctal plug included a biocompatible device with a corrective, cosmetic or therapeutic quality. A contact lens, for example, can provide one or more of: vision correcting functionality; cosmetic enhancement; and therapeutic effects. Each function is provided by a physical characteristic of the lens. A design incorporating a refractive quality into a lens can provide a vision corrective function. A pigment incorporated into the lens can provide a cosmetic enhancement. An active agent incorporated into a lens can provide a therapeutic functionality. Such physical characteristics are accomplished without the lens entering into an energized state.

More recently, it has been theorized that active components may be incorporated into a contact lens. Some components can include semiconductor devices. Some examples have shown semiconductor devices embedded in a contact lens placed upon animal eyes. However, such devices lack a free standing energizing mechanism. Although wires may be run from a lens to a battery to power such semiconductor devices, and it has been theorized that the devices may be wirelessly powered, no mechanism for such wireless power has been available.

It is desirable therefore to have ophthalmic lenses that are energized to an extent suitable for providing one or more of functionality into an ophthalmic lens and a controlled change in optical characteristic of an ophthalmic lens or other biomedical device.

SUMMARY OF THE INVENTION

Accordingly, the present invention includes an ophthalmic lens, with an energy source incorporated therein. In some embodiments, the energy source can provide an energized state that is capable of powering a semiconductor device. Some embodiments can also include a cast molded silicone hydrogel contact lens with a battery or other energy source contained within the ophthalmic lens in a biocompatible fashion. The energized portion may be thereby created via inclusion of a battery into the lens.

In some aspects of the present invention, an energized ophthalmic lens includes an energy source in contact with or embedded into a reactive monomer mix of the ophthalmic lens. More specifically, where the energy source, for example a battery, is contained or in connection with a stacked integrated component device.

Some embodiments of the present invention can additionally include a reenergizing component. The reenergizing component can further include a functional device, such as for example, a photoelectric device, a radio frequency absorbing device, an inductive energy coupling device, a capacitive energy coupling device, a thermoelectric device and a piezoelectric device.

In some embodiments, the energy source may placed within a cast molding system prior to polymerization of a reactive mixture also contained within the mold system. Lenses are formed via the control of actinic radiation to which the reactive monomer mixture is exposed.

DETAILED DESCRIPTION OF THE INVENTION

Figure 1:
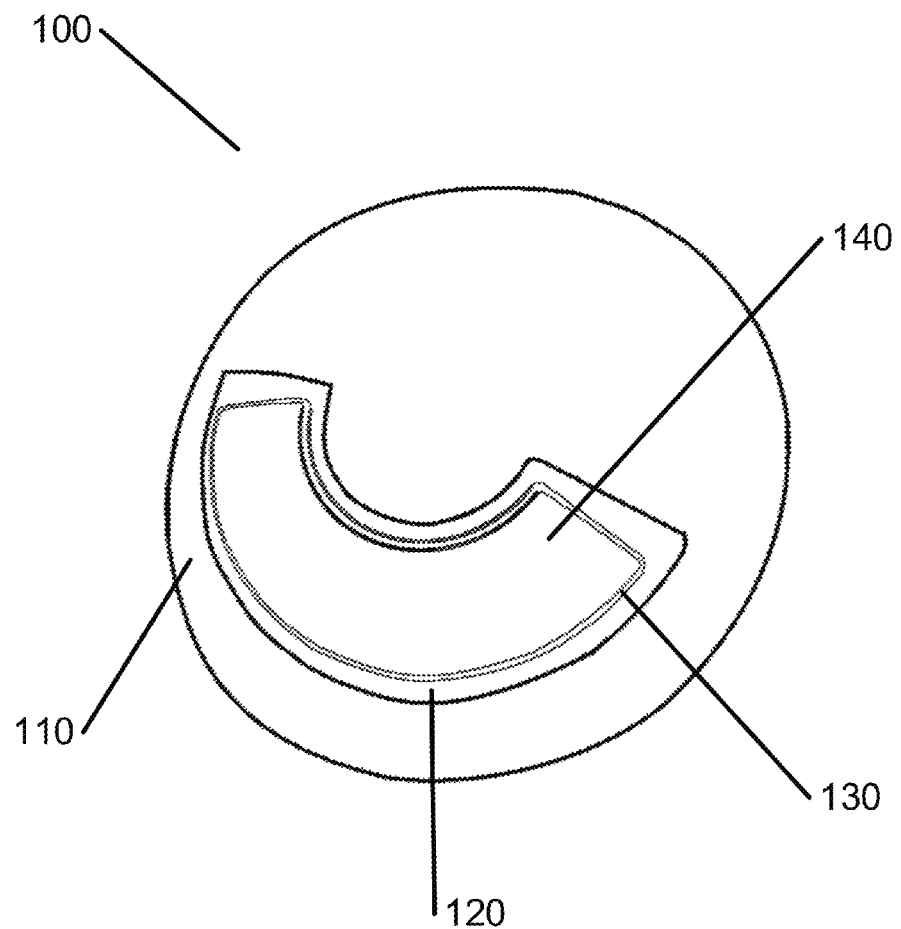
FIG. 1 illustrates an exemplary embodiment of an energized ophthalmic lens.

The present invention includes biomedical devices, such as ophthalmic lenses and in particular, the present invention includes an ophthalmic lens with an Energy Source incorporated therein. The description of both preferred and alternative embodiments are exemplary embodiments only, and it is understood that to those skilled in the art that variations, modifications and alterations may be apparent. It is therefore to be understood that said exemplary embodiments do not limit the scope of the underlying invention.

GLOSSARY

In this description and claims directed to the presented invention, various terms may be used for which the following definitions will apply:

Energized: The state of being able to supply electrical current to or to have electrical energy stored within.

Energized Ophthalmic Lens: An energized ophthalmic lens refers to an ophthalmic lens with an energy source added onto or embedded within the formed lens.

Energy: The capacity of a physical system to perform work. Many uses within this invention may relate to said capacity being able to perform electrical actions in doing work.

Energy Source: A device capable of supplying Energy or placing a biomedical device in an Energized state.

Energy Harvesters: A device capable of extracting energy from the environment and convert it to electrical energy.

Lens: As used herein "lens" refers to any ophthalmic device that resides in or on the eye. These devices can provide optical correction or may be cosmetic. For example, the term lens can refer to a contact lens, intraocular lens, overlay lens, ocular insert, optical insert or other similar device through which vision is corrected or modified, or through which eye physiology is cosmetically enhanced (e.g. iris color) without impeding vision. In some embodiments, the preferred lenses of the invention are soft contact lenses are made from silicone elastomers or hydrogels, which include but are not limited to silicone hydrogels.

Lens Forming Mixture: As used herein, the term "lens forming mixture" or "Reactive Mixture" or "RMM" (reactive monomer mixture) refers to a monomer or prepolymer material which can be cured and crosslinked or crosslinked to form an ophthalmic lens. Various embodiments can include lens forming mixtures with one or more additives such as: UV blockers, tints, photoinitiators or catalysts, and other additives one might desire in an ophthalmic lenses such as, contact or intraocular lenses.

Lithium Ion Cell: An electrochemical cell where Lithium ions move through the cell to generate electrical energy. This electrochemical cell, typically called a battery, may be reenergized or recharged in its typical forms.

Power: Work done or energy transferred per unit of time.

Rechargeable or Re-energizable: Capable of being restored to a state with higher capacity to do work. Many uses within this invention may relate to the capability of being restored with the ability to flow electrical current at a certain rate for a certain, reestablished time period.

Reenergize or Recharge: To restore to a state with higher capacity to do work. Many uses within this invention may relate to restoring a device to the capability to flow electrical current at a certain rate for a certain, reestablished time period.

"Stacked Integrated Component Devices" as used herein and sometimes referred to as "SIC-Devices", refers to the product of packaging technologies that can assemble thin layers of substrates, which may contain electrical and electromechanical devices, into operative integrated devices by means of stacking at least a portion of each layer upon each other. The layers may comprise component devices of various types, materials, shapes, and sizes. Furthermore, the layers may be made of various diverse production technologies to fit and assume various contours as it may be desired.

In general, in the present invention, an Energy Source is embedded at least partially within material formed into an ophthalmic lens. In some embodiments, an ophthalmic lens includes an optic zone through which a wearer of the lens sees. A pattern of components and an Energy Source can be located exterior to an optic zone. Other embodiments can include a pattern of conductive material and one or more Energy Sources which are small enough to not adversely affect the sight of a contact lens wearer and therefore can be located within, or exterior to, an optical zone.

In general, according to some embodiments of the present invention, an Energy Source is embodied within an ophthalmic lens Energized Ophthalmic Lens Device Referring now to FIG. 1, an energized lens 100 with an embedded Energy Source 140 is illustrated. In this example, a standard hydrogel formed ophthalmic lens is depicted as item 110. Embedded, or at least partially embedded within the formed hydrogel material 110 is an Energy Source 140. In some embodiments, this Energy Source 140 includes an electrochemical cell or battery as the storage means for the energy. Such a storage means may require effective means of encapsulation and isolation of the materials it is made from and the environment as illustrated by a sealed encapsulating layer 130. Some specific embodiments include a lithium ion battery. Lithium ion batteries are generally rechargeable. According to the present invention, the lithium ion battery is in electrical communication with a charging device and also a power management circuit, both of which are embedded within the lens.

Additionally, some embodiments may include a battery acting as an Energy Source 140 that is made of thin layers of materials. Such embodiments may therefore also include a flexible substrate to provide support for the thin film material 120. Numerous embodiments include various Energy Sources 140 and types, wherein each of the Energy Sources 140 Energize an ophthalmic lens.

Figure 6:
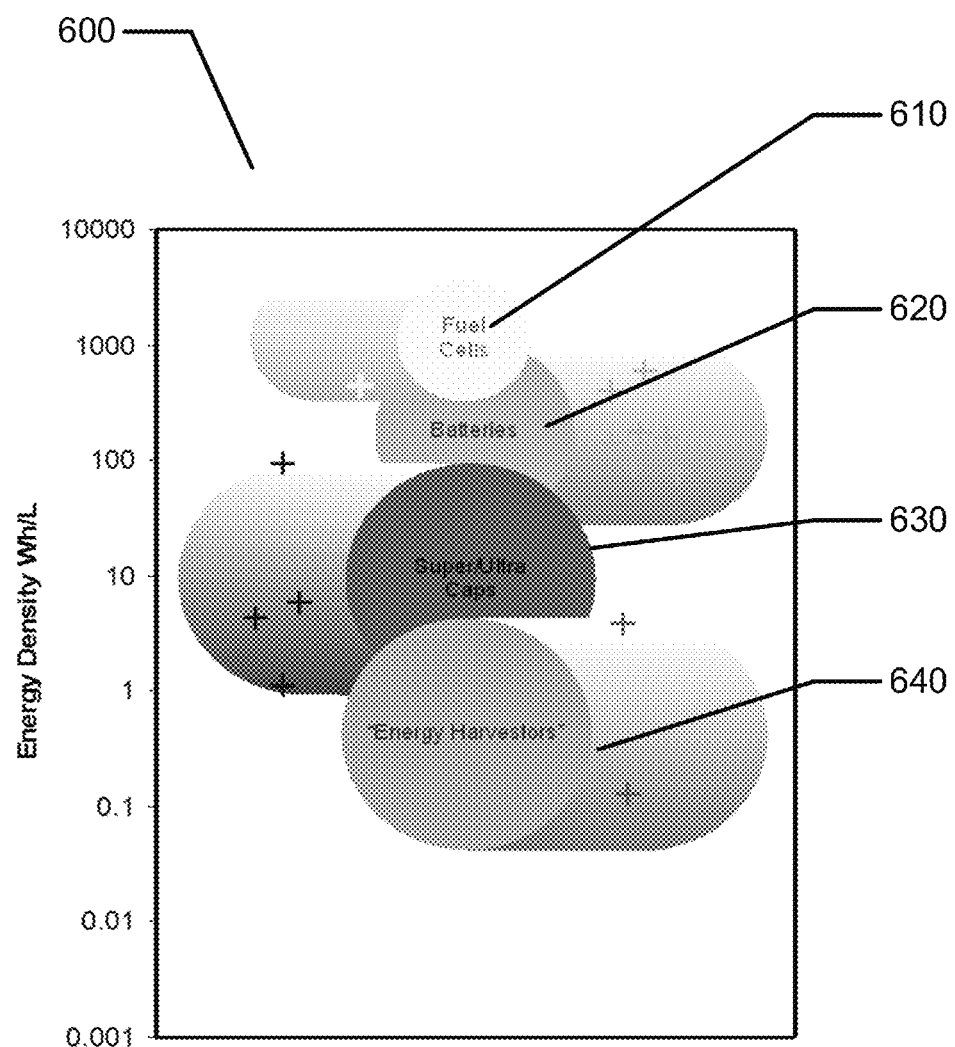
FIG. 6 illustrates a depiction of some exemplary types of energy sources ordered by estimates of the amount of energy that they may provide in ratio to their volume.

Referring now to FIG. 6, a view of some of the options that may be included in different types of Energy Sources 140 that may be embedded in an energized ophthalmic lens 100 is demonstrated in FIG. 6 as item 600. As previously mentioned, a set of embodiments of Energy Sources 140 can include batteries. Batteries are demonstrated in FIG. 6 as item 620. FIG. 6 also demonstrates a graph of the various options in order of the density of the energy that they can store. Batteries 600, for example, include a region of energy density from .about.50 to .about.800 Whr/L.

Referring now to graph 600, it can be seen that energy harvesters, item 640, do not exhibit high energy density. However, it may be apparent to one skilled in the art that there are other manners that energy harvesters embedded within a lens would have an advantage.

For example, energy harvesters can include photovoltaic energy cells, thermoelectric cells or piezoelectric cells. Such harvesters have a positive aspect in that they can absorb energy from the environment and then can provide electrical energy without a wired connection. In some embodiments, harvesters may comprise the source in an energized ophthalmic lens. In other embodiments, however, the energy harvester may be combined with other sources that can store energy in an electrical form.

Other types of Energy Source include the use of capacitor type devices, as shown in graph 600 as item 630. It may be apparent, that capacitors comprise an energy density solution that is higher than energy harvesters but less than that of batteries, item 620. Capacitors, nevertheless, have some inherent advantages.

Capacitors are a type of Energy Source that stores the energy in an electrical form and therefore, may be one of the Energy Sources combined with energy harvesters to create a wireless Energy Source that is capable of storage of energy. Generally, capacitors have an advantage over batteries in that they have higher power density, in general, than batteries. Capacitors that may be embedded in a silicone lens according to the present invention include: electrical thin film capacitors, Mylar capacitors, electrolytic capacitors and relative newer and more advanced technologies of high density nanoscale capacitors or supercapacitors.

In some additional embodiments, Energy Sources including electrochemical cells or batteries 620 may define a relatively desirable operational point. Batteries embedded within a silicone or other hydrogel have numerous advantageous characteristics. For example, Batteries store energy in a form that is directly converted to electrical energy. Some batteries may be rechargeable or Re-energizable and therefore, represent another category of Energy Source that may be coupled to energy harvesters. Batteries useful for the present invention will have relatively high energy density, the energy the batteries store can perform functions with reasonable energy requirements. In addition, in some embodiments, the batteries can be assembled into forms that are flexible. For applications requiring higher power capabilities, it may be apparent to one skilled in the art that a battery may also be coupled to capacitors. There may be numerous embodiments that comprise a battery at least as part of an Energy Source in an energized ophthalmic lens.

In additional embodiments a fuel cell is included as an Energy Source 610. Fuel cells generate electricity by consuming a chemical fuel source which then generates electricity and byproducts including heat energy. Fuel cell embodiments may be possible using biologically available materials as the fuel source.

The following discussions of the embodiments of this invention may focus generally on using a battery as the principle Energy Source of an energized ophthalmic lens. This focus should not limit the scope of the inventive art, as numerous Energy Sources including those that have been discussed may comprise embodiments of an energized ophthalmic lens.

As mentioned in some embodiments of the present invention the Energy Source includes an electrochemical cell or battery. There are many different types of batteries which may be included in embodiments of energized ophthalmic lenses. For example, single use batteries may be formed from various cathode and anode materials. By way of non-limiting examples these materials may include Zinc, carbon, Silver, Manganese, Cobalt, Lithium, Silicon. Still other embodiments may derive from the use of batteries that are rechargeable. Such batteries may in turn be made of Lithium Ion technology; Silver technology, Magnesium technology, Niobium technology. It may be apparent to one skilled in the art that various current battery technologies for single use or rechargeable battery systems may comprise the Energy Source in various embodiments of an energized ophthalmic lens.

The physical and dimensional constraints of a contact lens environment may favor certain battery types over others. An example of such favorability may occur for thin film batteries. Thin film batteries may occupy the small volume of space consistent with human ophthalmic embodiments. Furthermore, they may be formed upon a substrate that is flexible allowing for the body of both the ophthalmic lens and included battery with substrate to have freedom to flex.

In the case of thin film batteries, examples may include single charge and rechargeable forms. Rechargeable batteries afford the ability of extended usable product lifetime and, therefore, higher energy consumption rates. Much development activity has focused on the technology to produce electrically energized ophthalmic lenses with rechargeable thin film batteries; however, the inventive art is not limited to this subclass.

Rechargeable thin film batteries are commercially available, for example, Oak Ridge National Laboratory has produced various forms since the early 1990s. Current commercial producers of such batteries include Excellatron Solid State, LLC (Atlanta, Ga.), Infinite Power Solutions (Littleton, Colo.), and Cymbet Corporation, (Elk River, Minn.). The technology is currently dominated by uses that include flat thin film batteries. Use of such batteries may comprise some embodiments of this inventive art; however, forming the thin film battery into a three dimensional shape, for example with a spherical radius of curvature comprises desirable embodiments of the inventive art. It may be clear to one skilled in the art that numerous shapes and forms of such a three dimensional battery embodiment are within the scope of the invention.

In FIGS. 5a, 5b, 5c and 5d are numerous examples of different shapes that an Energy Source in an ophthalmic lens may take. Item 500 shows a reference Energy Source made of thin film materials, which for reference is formed as a flat shape. When the dimension of such a shape 500 is approximately a millimeter or less, it may comprise an Energy Source for an energized ophthalmic lens. Item 510 shows an exemplary three dimensional form where the flexible substrate and encapsulated battery assume a full annular shape, which when not flexibly distorted is roughly the same shape that an undistorted ophthalmic lens may assume. In some embodiments, the radius of the annular shape may approximate eight millimeters for an energized ophthalmic lens embodiment. The same three-dimensional aspect may be shared by embodiments which are quarter annulus 530, half annulus 520 or other arcuate shape. It may be apparent to one skilled in the arts that many different shapes including other partial annular shapes may comprise alternative embodiments within the scope of this invention. In some embodiments, rectangular, planar shapes may also be fit into a semi-spherical shell geometry included in an ophthalmic lens.

Another set of embodiments of the present invention relate to specific battery chemistries which may be advantageously utilized in an energized ophthalmic lens. An example embodiment, which was developed by Oak Ridge Laboratories, comprises constituents of a Lithium or Lithium-Ion Cell. Common materials for the anode of such cells include Lithium metal or alternatively for the Lithium Ion Cell include graphite. An example alternative embodiment of these cells includes be the incorporation of microscaled silicon features to act as the anode of such a thin film battery incorporated into a contact lens.

The materials used for the cathode of the batteries used in this novel art as well include multiple materials options. Common cathode materials include Lithium Manganese Oxide and Lithium Cobalt Oxide which have good performance metrics for the batteries thus formed. Alternatively, Lithium Iron Phosphide cathodes, can have similar performance, however, may in some applications have improved aspects relating to charging. As well, the dimension of these and other cathode materials can improve charging performance; as for example, forming the cathode from nanoscaled crystals of the various materials can dramatically improve the rate that the battery may be recharged at.

Various materials that may be included as constituents of an Energy Source may be preferably encapsulated. It may be desirable to encapsulate the Energy Source to generally isolate its constituents from entering the ophthalmic environment. Alternatively, aspects of the ophthalmic environment may negatively affect the performance of Energy Sources if they are not properly isolated by an encapsulation embodiment. Various embodiments of the inventive art may derive from the choice of materials.

Accordingly, in some embodiments, a lens material can include a silicone containing component. A "silicone-containing component" is one that contains at least one [—Si—O—] unit in a monomer, macromer or prepolymer. Preferably, the total Si and attached O are present in the silicone-containing component in an amount greater than about 20 weight percent, and more preferably greater than 30 weight percent of the total molecular weight of the silicone-containing component. Useful silicone-containing components preferably comprise polymerizable functional groups such as acrylate, methacrylate, acrylamide, methacrylamide, vinyl, N-vinyl lactam, N-vinylamide, and styryl functional groups.

Suitable silicone containing components include compounds of Formula I

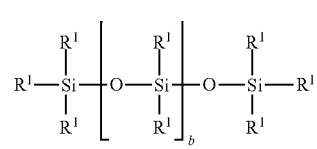

where

R.sup.1 is independently selected from monovalent reactive groups, monovalent alkyl groups, or monovalent aryl groups, any of the foregoing which may further comprise functionality selected from hydroxy, amino, oxa, carboxy, alkyl carboxy, alkoxy, amido, carbamate, carbonate, halogen or combinations thereof; and monovalent siloxane chains comprising 1-100 Si—O repeat units which may further comprise functionality selected from alkyl, hydroxy, amino, oxa, carboxy, alkyl carboxy, alkoxy, amido, carbamate, halogen or combinations thereof;

where b=0 to 500, where it is understood that when b is other than 0, b is a distribution having a mode equal to a stated value;

wherein at least one R.sup.1 comprises a monovalent reactive group, and in some embodiments between one and 3 R.sup.1 comprise monovalent reactive groups.

As used herein "monovalent reactive groups" are groups that can undergo free radical and/or cationic polymerization. Non-limiting examples of free radical reactive groups include (meth)acrylates, styryls, vinyls, vinyl ethers, C.sub.1-6alkyl(meth)acrylates, (meth)acrylamides, C.sub.1-6alkyl(meth)acrylamides, N-vinyllactams, N-vinylamides, C.sub.2-12alkenyls, C.sub.2-12alkenylphenyls, C.sub.2-12alkenylnaphthyls, C.sub.2-6alkenylphenylC.sub.1-6alkyls, O-vinylcarbamates and O-vinylcarbonates. Non-limiting examples of cationic reactive groups include vinyl ethers or epoxide groups and mixtures thereof. In one embodiment the free radical reactive groups comprises (meth)acrylate, acryloxy, (meth)acrylamide, and mixtures thereof.

Suitable monovalent alkyl and aryl groups include unsubstituted monovalent C.sub.1 to C.sub.16alkyl groups, C.sub.6-C.sub.14 aryl groups, such as substituted and unsubstituted methyl, ethyl, propyl, butyl, 2-hydroxypropyl, propoxypropyl, polyethyleneoxypropyl, combinations thereof and the like.

In one embodiment b is zero, one R.sup.1 is a monovalent reactive group, and at least 3 R.sup.1 are selected from monovalent alkyl groups having one to 16 carbon atoms, and in another embodiment from monovalent alkyl groups having one to 6 carbon atoms. Non-limiting examples of silicone components of this embodiment include 2-methyl-2-hydroxy-3-[3-[1,3,3,3-tetramethyl-1-[(trimethylsilyl)oxy]disil-oxanyl]propoxy]propyl ester ("SiGMA"), 2-hydroxy-3-methacryloxypropyloxypropyl-tris(trimethylsiloxy) silane, 3-methacryloxypropyltris(trimethylsiloxy)silane ("TRIS"), 3-methacryloxypropylbis(trimethylsiloxy)methylsilane and 3-methacryloxypropylpentamethyl disiloxane.

In another embodiment, b is 2 to 20, 3 to 15 or in some embodiments 3 to 10; at least one terminal R.sup.1 comprises a monovalent reactive group and the remaining R.sup.1 are selected from monovalent alkyl groups having 1 to 16 carbon atoms, and in another embodiment from monovalent alkyl groups having 1 to 6 carbon atoms. In yet another embodiment, b is 3 to 15, one terminal R.sup.1 comprises a monovalent reactive group, the other terminal R.sup.1 comprises a monovalent alkyl group having 1 to 6 carbon atoms and the remaining R.sup.1 comprise monovalent alkyl group having 1 to 3 carbon atoms. Non-limiting examples of silicone components of this embodiment include (mono-(2-hydroxy-3-methacryloxypropyl)-propyl ether terminated polydimethylsiloxane (400-1000 MW)) ("OH-mPDMS"), monomethacryloxypropyl terminated mono-n-butyl terminated polydimethylsiloxanes (800-1000 MW), ("mPDMS").

In another embodiment b is 5 to 400 or from 10 to 300, both terminal R.sup.1 comprise monovalent reactive groups and the remaining R.sup.1 are independently selected from monovalent alkyl groups having 1 to 18 carbon atoms which may have ether linkages between carbon atoms and may further comprise halogen.

In one embodiment, where a silicone hydrogel lens is desired, the lens of the present invention will be made from a reactive mixture comprising at least about 20 and preferably between about 20 and 70% wt silicone containing components based on total weight of reactive monomer components from which the polymer is made.

In another embodiment, one to four R.sup.1 comprises a vinyl carbonate or carbamate of the formula:

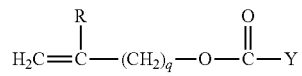

wherein:

Y denotes O—, S— or NH—; R denotes, hydrogen or methyl; d is 1, 2, 3 or 4; and q is 0 or 1.

The silicone-containing vinyl carbonate or vinyl carbamate monomers specifically include: 1,3-bis[4-(vinyloxycarbonyloxy)but-1-yl]tetramethyl-disiloxane; 3-(vinyloxycarbonylthio) propyl-[tris(trimethylsiloxy)silane]; 3-[tris(trimethylsiloxy)silyl]propyl allyl carbamate; 3-[tris(trimethylsiloxy)silyl]propyl vinyl carbamate; trimethylsilylethyl vinyl carbonate; trimethylsilylmethyl vinyl carbonate, and

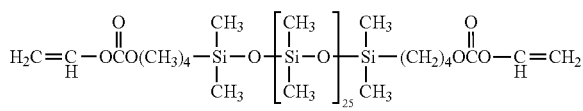

Where biomedical devices with modulus below about 200 are desired, only one R.sup.1 shall comprise a monovalent reactive group and no more than two of the remaining R.sup.1 groups will comprise monovalent siloxane groups.

Another class of silicone-containing components includes polyurethane macromers of the following formulae:

(*D*A*D*G).sub.a*D*D*E.sup.1;

E(*D*G*D*A).sub.a*D*G*D*E.sup.1 or;

E(*D*A*D*G).sub.a*D*A*D*E.sup.1 Formulae IV-VI wherein:

D denotes an alkyl diradical, an alkyl cycloalkyl diradical, a cycloalkyl diradical, an aryl diradical or an alkylaryl diradical having 6 to 30 carbon atoms, G denotes an alkyl diradical, a cycloalkyl diradical, an alkyl cycloalkyl diradical, an aryl diradical or an alkylaryl diradical having 1 to 40 carbon atoms and which may contain ether, thio or amine linkages in the main chain;

* denotes a urethane or ureido linkage;

.sub.a is at least 1;

A denotes a divalent polymeric radical of formula:

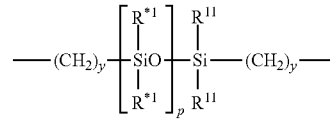

R.sup.11 independently denotes an alkyl or fluoro-substituted alkyl group having 1 to 10 carbon atoms which may contain ether linkages between carbon atoms; y is at least 1; and p provides a moiety weight of 400 to 10,000; each of E and E.sup.1 independently denotes a polymerizable unsaturated organic radical represented by formula:

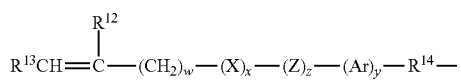

wherein: R.sup.12 is hydrogen or methyl; R.sup.13 is hydrogen, an alkyl radical having 1 to 6 carbon atoms, or a —CO—Y—R.sup.15 radical wherein Y is —O—, Y—S— or —NH—; R.sup.14 is a divalent radical having 1 to 12 carbon atoms; X denotes —CO— or —OCO—; Z denotes —O— or —NH—; Ar denotes an aromatic radical having 6 to 30 carbon atoms; w is 0 to 6; x is 0 or 1; y is 0 or 1; and z is 0 or 1.

A preferred silicone-containing component is a polyurethane macromer represented by

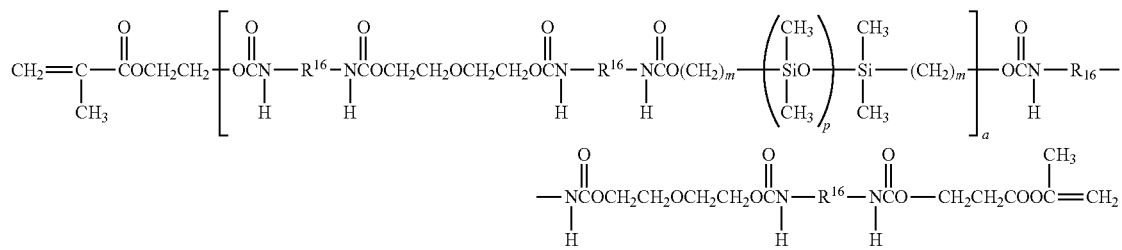

the following formula:

wherein R.sup.16 is a diradical of a diisocyanate after removal of the isocyanate group, such as the diradical of isophorone diisocyanate. Another suitable silicone containing macromer is compound of formula X (in which x+y is a number in the range of 10 to 30) formed by the reaction of fluoroether, hydroxy-terminated polydimethylsiloxane, isophorone diisocyanate and isocyanatoethylmethacrylate.

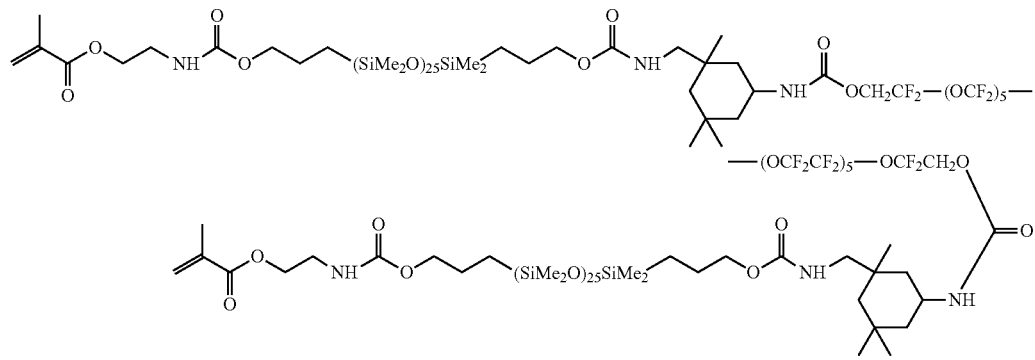

Other silicone containing components suitable for use in this invention include macromers containing polysiloxane, polyalkylene ether, diisocyanate, polyfluorinated hydrocarbon, polyfluorinated ether and polysaccharide groups; polysiloxanes with a polar fluorinated graft or side group having a hydrogen atom attached to a terminal difluoro-substituted carbon atom; hydrophilic siloxanyl methacrylates containing ether and siloxanyl linkages and crosslinkable monomers containing polyether and polysiloxanyl groups. Any of the foregoing polysiloxanes can also be used as the silicone containing component in this invention.

In some embodiments, a binding layer can be utilized to position an Energy Source within a mold part used to form an ophthalmic lens. The binding polymer can be capable of forming an interpenetrating polymer network with a lens material, the need for formation of covalent bonds between the binder and lens material to form a stable lens is eliminated. Stability of a lens with an Energy Source placed into the binder is provided by entrapment of the Energy Source in the binding polymer and the lens base polymer. The binding polymers of the invention can include, for example, those made from a homopolymer or copolymer, or combinations thereof, having similar solubility parameters to each other and the binding polymer has similar solubility parameters to the lens material. Binding polymers may contain functional groups that render the polymers and copolymers of the binding polymer capable of interactions with each other. The functional groups can include groups of one polymer or copolymer interact with that of another in a manner that increases the density of the interactions helping to inhibit the mobility of and/or entrap the pigment particles. The interactions between the functional groups may be polar, dispersive, or of a charge transfer complex nature. The functional groups may be located on the polymer or copolymer backbones or be pendant from the backbones.

By way of non-limiting example, a monomer, or mixture of monomers, that form a polymer with a positive charge may be used in conjunction with a monomer or monomers that form a polymer with a negative charge to form the binding polymer. As a more specific example, methacrylic acid ("MAA") and 2-hydroxyethylmethacrylate ("HEMA") may be used to provide a MAA/HEMA copolymer that is then mixed with a HEMA/3-(N,N-dimethyl) propyl acrylamide copolymer to form the binding polymer.

As another example, the binding polymer may be composed of hydrophobically-modified monomers including, without limitation, amides and esters of the formula:

CH.sub.3(CH.sub.2).sub.x-L-COCHR.dbd.CH.sub.2 wherein L may be —NH or oxygen, x may be a whole number from 2 to 24, R may be a C.sub.1 to C.sub.6 alkyl or hydrogen and preferably is methyl or hydrogen. Examples of such amides and esters include, without limitation, lauryl methacrylamide, and hexyl methacrylate. As yet another example, polymers of aliphatic chain extended carbamates and ureas may be used to form the binding polymer.

Binding polymers suitable for a binding layer may also include a random block copolymer of HEMA, MAA and lauryl methacrylate ("LMA"), a random block copolymer of HEMA and MAA or HEMA and LMA, or a homopolymer of HEMA. The weight percentages, based on the total weight of the binding polymer, of each component in these embodiments is about 93 to about 100 weight percent HEMA, about 0 to about 2 weight percent MAA, and about 0 to about 5 weight percent LMA.

The molecular weight of the binding polymer can be such that it is somewhat soluble in the lens material and swells in it. The lens material diffuses into the binding polymer and is polymerized and/or cross-linked. However, at the same time, the molecular weight of the binding polymer cannot be so high as to impact the quality of the printed image. Preferably, the molecular weight of the binding polymer is about 7,000 to about 100,000, more preferably about 7,000 to about 40,000, most preferably about 17,000 to about 35,000 M.sub.peak which corresponds to the molecular weight of the highest peak in the SEC analyses (=(M.sub.n.times.M.sub.w).sup.1/2)

For purposes of the invention, the molecular weight can be determined using a gel permeation chromatograph with a 90.degree. light scattering and refractive index detectors. Two columns of PW4000 and PW2500, a methanol-water eluent of 75/25 wt/wt adjusted to 50 mM sodium chloride and a mixture of polyethylene glycol and polyethylene oxide molecules with well defined molecular weights ranging from 325,000 to 194 are used.

One ordinarily skilled in the art will recognize that, by using chain transfer agents in the production of the binding polymer, by using large amounts of initiator, by using living polymerization, by selection of appropriate monomer and initiator concentrations, by selection of amounts and types of solvent, or combinations thereof, the desired binding polymer molecular weight may be obtained. Preferably, a chain transfer agent is used in conjunction with an initiator, or more preferably with an initiator and one or more solvents to achieve the desired molecular weight. Alternatively, small amounts of very high molecular weight binding polymer may be used in conjunction with large amounts of solvent to maintain a desired viscosity for the binding polymer. Preferably, the viscosity of the binding polymer will be about 4,000 to about 15,000 centipoise at 23.degree. C.

Chain transfer agents useful in forming the binding polymers used in the invention have chain transfer constants values of greater than about 0.01, preferably greater than about 7, and more preferably greater than about 25,000.

Any desirable initiators may be used including, without limitation, ultra-violet, visible light, thermal initiators and the like and combinations thereof. Preferably, a thermal initiator is used, more preferably 2,2-azobis isobutyronitrile and 2,2-azobis 2-methylbutyronitrile. The amount of initiator used will be about 0.1 to about 5 weight percent based on the total weight of the formulation. Preferably, 2,2-azobis 2-methylbutyronitrile is used with dodecanethiol.

A binding polymer layer or other media may be made by any convenient polymerization process including, without limitation, radical chain polymerization, step polymerization, emulsion polymerization, ionic chain polymerization, ring opening, group transfer polymerization, atom transfer polymerization, and the like. Preferably, a thermal-initiated, free-radical polymerization is used. Conditions for carrying out the polymerization are within the knowledge of one ordinarily skilled in the art.

Solvents useful in the production of the binding polymer are medium boiling solvents having boiling points between about 120 and 230.degree. C. Selection of the solvent to be used will be based on the type of binding polymer to be produced and its molecular weight. Suitable solvents include, without limitation, diacetone alcohol, cyclohexanone, isopropyl lactate, 3-methoxy 1-butanol, 1-ethoxy-2-propanol, and the like.

In some embodiments, a binding polymer layer 111 of the invention may be tailored, in terms of expansion factor in water, to the lens material with which it will be used. Matching, or substantially matching, the expansion factor of the binding polymer with that of the cured lens material in packing solution may facilitate the avoidance of development of stresses within the lens that result in poor optics and lens parameter shifts. Additionally, the binding polymer can be swellable in the lens material, permitting swelling of the image printed using the colorant of the invention. Due to this swelling, the image becomes entrapped within the lens material without any impact on lens comfort.

In some embodiments, colorants may be included in the binding layer. Pigments useful with the binding polymer in the colorants of the invention are those organic or inorganic pigments suitable for use in contact lenses, or combinations of such pigments. The opacity may be controlled by varying the concentration of the pigment and opacifying agent used, with higher amounts yielding greater opacity. Illustrative organic pigments include, without limitation, pthalocyanine blue, pthalocyanine green, carbazole violet, vat orange #1, and the like and combinations thereof. Examples of useful inorganic pigments include, without limitation, iron oxide black, iron oxide brown, iron oxide yellow, iron oxide red, titanium dioxide, and the like, and combinations thereof. In addition to these pigments, soluble and non-soluble dyes may be used including, without limitation, dichlorotriazine and vinyl sulfone-based dyes. Useful dyes and pigments are commercially available.

Colors may be arranged for example in a pattern to mask components present in a lens according to the present invention. For example, opaque colors can simulate the appearance of a natural eye and cover up the presence of components within a lens.

In addition, in some embodiments, the binding layer contains one or more solvents that aid in coating of the binding layer onto the mold part. It is another discovery of the invention that, to facilitate a binding layer that does not bleed or run on the mold part surface to which it is applied, it is desirable, and preferred, that the binding layer have a surface tension below about 27 mN/m. This surface tension may be achieved by treatment of the surface, for example a mold surface, to which the binding layer will be applied. Surface treatments may be effected by methods known in the art, such as, but not limited to plasma and corona treatments. Alternatively, and preferably, the desired surface tension may be achieved by the choice of solvents used in the colorant.

Accordingly, exemplary solvents useful in the binding layer include those solvents that are capable of increasing or decreasing the viscosity of the binding layer and aiding in controlling the surface tension. Suitable solvents include, without limitation, cyclopentanones, 4-methyl-2-pentanone, 1-methoxy-2-propanol, 1-ethoxy-2-propanol, isopropyl lactate and the like and combinations thereof. Preferably, 1-ethoxy-2-propanol and isopropyl lactate are used.

In some preferred embodiments, at least three different solvents are used in the binding layer material of the invention. The first two of these solvents, both medium boiling point solvents, are used in the production of the binding polymer. Although these solvents may be stripped from the binding polymer after its formation, it is preferred that they are retained. Preferably, the two solvents are 1-ethoxy-2-propanol and isopropyl lactate. An additional low boiling solvent, meaning a solvent the boiling point of which is between about 75 and about 120.degree. C., can be used to decrease the viscosity of the colorant as desired. Suitable low boiling solvents include, without limitation, 2-propanol, 1-methoxy-2-propanol, 1-propanol, and the like and combinations thereof. Preferably, 1-propanol is used.

The specific amount of solvents used can depend on a number of factors. For example, the amount of solvents used in forming the binding polymer will depend upon the molecular weight of the binding polymer desired and the constituents, such as the monomers and copolymers, used in the binding polymer. The amount of low boiling solvent used will depend upon the viscosity and surface tension desired for the colorant. Further, if the colorant is to be applied to a mold and cured with a lens material, the amount of solvent used will depend upon the lens and mold materials used and whether the mold material has undergone any surface treatment to increase its wettability. Determination of the precise amount of solvent to be used is within the skill of one ordinarily skilled in the art. Generally, the total weight of the solvents used will be about 40 to about 75 weight percent of solvent will be used.

In addition to the solvents, a plasticizer may be and, preferably is, added to the binding layer to reduce cracking during the drying of the binding layer and to enhance the diffusion and swelling of the binding layer by the lens material. The type and amount of plasticizer used will depend on the molecular weight of the binding polymer used and, for colorants placed onto molds that are stored prior to use, the shelf-life stability desired. Useful plasticizers include, without limitation, glycerol, propylene glycol, dipropylene glycol, tripropylene glycol, polyethylene glycol 200, 400, or 600, and the like and combinations thereof. Preferably, glycerol is used. Amounts of plasticizer used generally will be 0 to about 10 weight percent based on the weight of the colorant.

One ordinarily skilled in the art will recognize that additives other than those discussed also may be included in the binding layer composition of the invention. Suitable additives include, without limitation, additives that aid flow and leveling, additives for foam prevention, additives for rheology modification, and the like, and combinations thereof.

In some embodiments of the present invention, the binding layer becomes embedded in the lens material upon curing of the lens material. Thus, the binding layer may embed closer to the front or back surface of the lens formed depending on the surface of the mold to which the lens the binding layer is applied. Additionally, one or more layers of binding layer may be applied in any order.

Although invention may be used to provide hard or soft contact lenses made of any known lens material, or material suitable for manufacturing such lenses, preferably, the lenses of the invention are soft contact lenses having water contents of about 0 to about 90 percent. More preferably, the lenses are made of monomers containing hydroxy groups, carboxyl groups, or both or be made from silicone-containing polymers, such as siloxanes, hydrogels, silicone hydrogels, and combinations thereof. Material useful for forming the lenses of the invention may be made by reacting blends of macromers, monomers, and combinations thereof along with additives such as polymerization initiators. Suitable materials include, without limitation, silicone hydrogels made from silicone macromers and hydrophilic monomers.

Additional embodiments may come from the nature in which the internal components are encapsulated by the encapsulating material. It may be possible to coat an Energy Source in a manner that involves a seam between two layers of encapsulant. Alternatively the encapsulant may be applied in such a manner to not generate seams, although it should be noted that many embodiments require the Energy Source to provide two distinct and isolated electrical contact points. It may be obvious to one skilled in the art that there are various other means to encapsulate an Energy Source which may be consistent with the art detailed herein.

Figure 2:
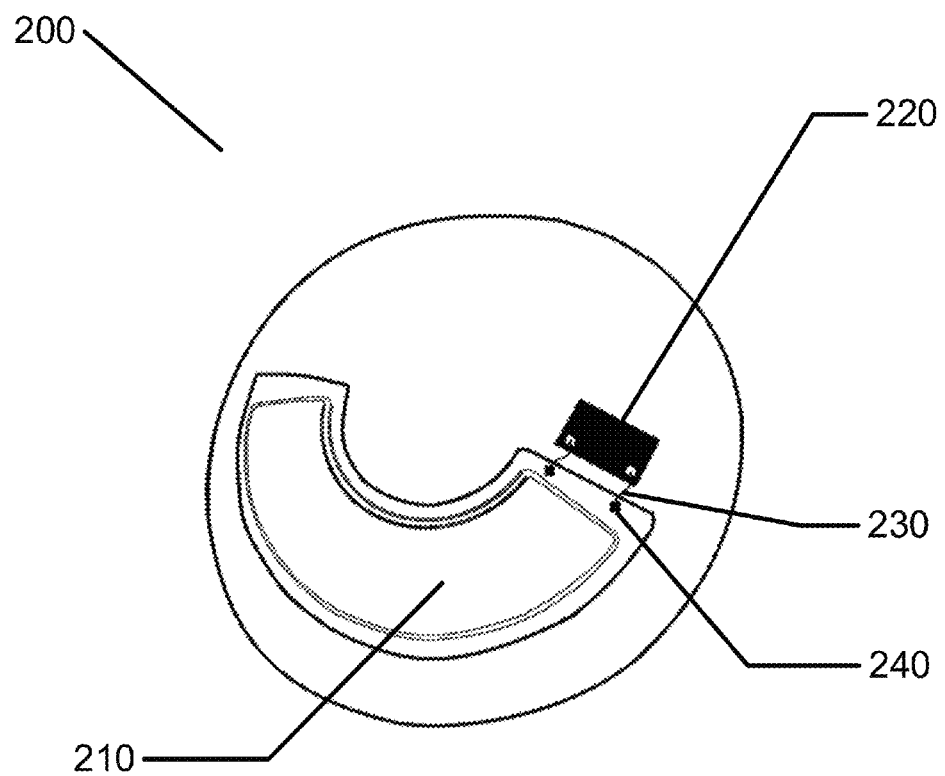
FIG. 2 illustrates an exemplary embodiment of an energized ophthalmic lens including a device for reenergization.

As mentioned, an Energy Source in some embodiments may need to provide energy in an electrical form and therefore have at least two electrically isolated contact points to connect the Energy Source to an element that is being energized. In some embodiments two electrically conductive bonding pads may be cut or otherwise formed into the encapsulant. To these bond pads electrical conduits of some form may be affixed to allow the electrical energy to flow from the source to the device to be energized. Referring now to FIG. 2, item 200 demonstrates how an Energy Source 210 may have two contact points 240. These contact points may have two electrically conductive wires 230 affixed to them to conduct the energy from the Energy Source 210 to another device 220.

The manner by which the electrical wires 230 may be connected to the contact points 240 may form numerous embodiments within this art. In some embodiments, these wires may be affixed by a wire bonding technique which will physically scrub a wire into an electrical contact with an alternative bond pad metal. Still other embodiments may derive from melting a contacting metallurgy between the wire 230 and the contact point 240 for example with a solder technique. It may be possible in other embodiments to evaporatively deposit the connecting wires 230 to the contact point 240. In still other embodiments, conductive epoxies or inks may be used to define the conducting element 230 and to connect it to the contact pad 240. It may be obvious to one skilled in the art that numerous means of making a connection to the contact point of an Energy Source to convey energy to or from another device may comprise embodiments within the scope of this invention.

As previously discussed and demonstrated in FIG. 2, item 200, the Energy Source may be defined as a composite of two or more of the types of Energy Sources that have been described. For example, the Energy Source in FIG. 2 may be comprised of a rechargeable lithium ion thin film battery 210 that is combined with a photocell 240. Numerous photocell types may be consistent with the art herein, as an example a photovoltaic device that is used for such embodiments is the CPC1822 manufactured by Clare, Inc. (Beverly, Mass.), which measures approximately 2.5 mm.times.1.8 mm.times.0.3 mm in die form and is capable of providing 4 volts of direct current electricity (VDC) in light conditions. In some embodiments, the output of the photovoltaic device may be directly provided to the battery as demonstrated in FIG. 2. Alternatively, a power management device may control the charging of the rechargeable battery with a reenergizing device of some kind. This specific example is provided in a non-limiting sense as there may be numerous embodiments of reenergizing an Energy Source within the scope of this inventive art on energized ophthalmic lenses.

In the case of the Clare photovoltaic cell, an external light source may comprise the manner to reenergize another attached Energy Source. In light intensities on the order of one sun or more, the cell provides significant charging current. There may be numerous manners to configure a reenergizing system to interact with such a photovoltaic device. By nonlimiting example, it may be possible to provide light of appropriate intensity during the storage of an ophthalmic lens in hydration media.

Other embodiments of reenergizing an Energy Source may be defined by alternative devices. For example, a thermal gradient across the ophthalmic lens body may be used by a thermoelectric device to provide reenergization to an Energy Source. In alternative embodiments, external energy may be coupled into the ophthalmic lens with use of an external radiofrequency signal and an absorbing device in the lens; an external voltage field and a capacitive coupling device in the lens; or mechanical energy or pressure and a piezoelectric device. It may be obvious to one skilled in the art that there may be numerous manners of reenergizing an Energy Source in an energized ophthalmic lens.

As mentioned in the earlier discussion, non-rechargeable chemistries of battery type Energy Sources may provide alternative embodiments of the novelty disclosed herein. While potentially lacking some of the advantages of rechargeability, such embodiments may alternatively have potential cost and implementation advantages. It may be considered within the scope of this disclosure to include non-rechargeable encapsulated electrochemical cells in equivalent manners to the rechargeable Energy Sources that have been disclosed herein.

The various Energy Sources of the present invention provide an "on board" power source within the ophthalmic lens which may be used in conjunction with electronic components, flexible circuit interconnect substrates, printed electrical interconnects, sensors, and/or other custom active components. These various components that may be energized may define embodiments that perform a broad range of functions. By way of non-limiting examples, an energized ophthalmic lens may be an electro-optic device energizing functionality to adjust the focal characteristics of an ophthalmic lens. In still other embodiments, the energized function may activate a pumping mechanism within the ophthalmic lens that may pump pharmaceuticals or other materials. Still further energized function may involve sensing devices and communication devices within an ophthalmic lens. It may be obvious to one skill in the art that there are an abundant range of embodiments relating to the function that may be enabled within an energized ophthalmic lens.

In some embodiments the Energy Source within an energized ophthalmic lens may energize a control function within the ophthalmic lens to provide for the wireless, controlled activation of still further energized function within an ophthalmic lens or other shaped hydrogel article. By way of non-limiting example, the Energy Source may comprise an embedded encapsulated thin film microbattery which may have a finite, limited maximum current capacity.

In order to minimize leakage currents, or quiescent current draw so that a fully charged thin film microbattery will maintain its charge as long as possible during storage, various means to activate or electrically connect the microbattery to other components within the electroactive lens may be utilized. In some embodiments, a photovoltaic cell (e.g. Clare CPC1822 in die form) or a photoelectric sensing device may activate transistors or other microelectronic components within the lens under prescribed lighting conditions that are then activate the interconnection of the battery with other microelectronic components within the lens. In another embodiment, a micro-sized hall-effect sensor/switch such as the A1172 manufactured by Allegro Microsystems, Inc. (Worcester, Mass.) may be used to activate the battery and/or other microelectronic components within the lens when exposed to a north and/or south pole of a magnet. In other embodiments, physical contact switches, membrane switches, RF switches, temperature sensors, photodiodes, photoresistors, phototransistors, or optical sensors may be used to activate the battery and/or attached electronics within the energized ophthalmic lens.

In some embodiments an Energy Source within an energized ophthalmic lens may be incorporated alongside integrated circuits. In exemplary embodiments of this type, incorporation of planar thin film microbatteries on silicon substrates are incorporated into the semiconductor fabrication process. Such approaches may provide separate power sources for various integrated circuits which may be incorporated into the electroactive lens of the present invention. In alternative embodiments the integrate circuit may be incorporated as a distinct component of the energized lens.

Figure 3:
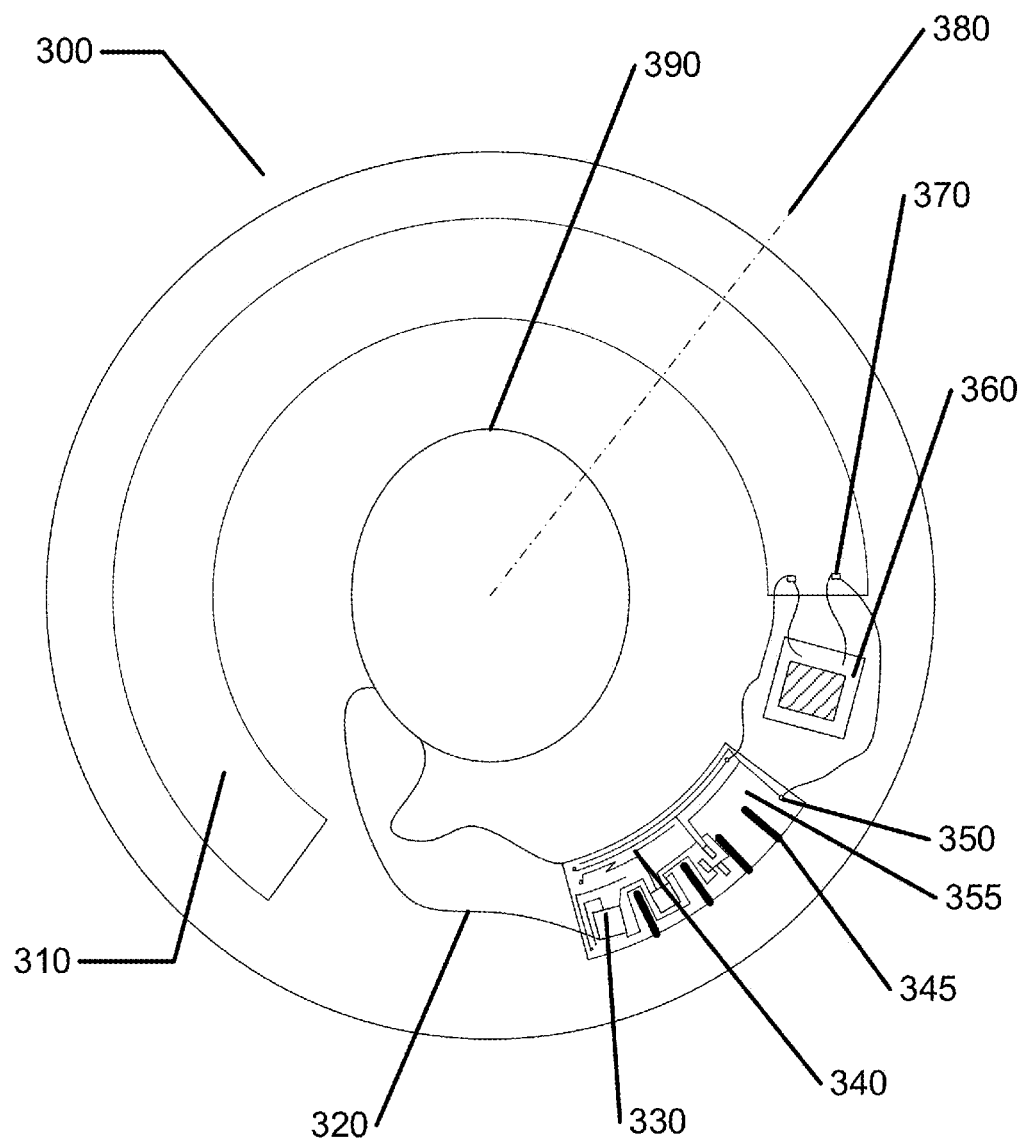
FIG. 3 illustrates an example of an energized ophthalmic lens with a device for reenergization and an energized component.

Referring to FIG. 3, item 300 a depiction of an exemplary embodiment of an energized ophthalmic lens is shown. In this depiction, the Energy Source 310 may include a thin film, rechargeable lithium ion battery. The battery may have contact points 370 to allow for interconnection. Wires may be wire bond wires to the contact points 370 and connect the battery to a photoelectric cell 360 which may be used to reenergize the battery Energy Source 310. Additional wires may connect the Energy Source to a flexible circuit interconnect via wire bonded contacts on a second set of contact points 350. These contact points 350 may be a portion of a flexible interconnect substrate 355. This interconnect substrate may be formed into a shape approximating a typical lens form in a similar manner to the Energy Source previously discussed. To add additional flexibility, an interconnect substrate 355 may include additional shape features such as radial cuts 345 along its length. On individual flaps of the interconnect substrate 355 may be connected various electronic components like ICs, discrete components, passive components and such devices which are shown as item 330. These components are interconnected by wires or other connection means 340 to the conduction paths within the interconnect substrate 355. By way of non-limiting example, the various components may be connected to the flexible interconnect substrate 355 by the various means that interconnections to the battery already discussed may be made. The combination of the various electrical components may define a control signal for an electro-optical device shown as item 390. This control signal may be conducted along interconnect 320. This type of exemplary energized ophthalmic lens with energized function is provided only for the purpose of example. In no way should this description be construed to limit the scope of the inventive art as it may be apparent to one skilled in the arts that many different embodiments of function, design, interconnection scheme, energization scheme and overall utilization of the concepts of this invention may exist.

Figure 4:
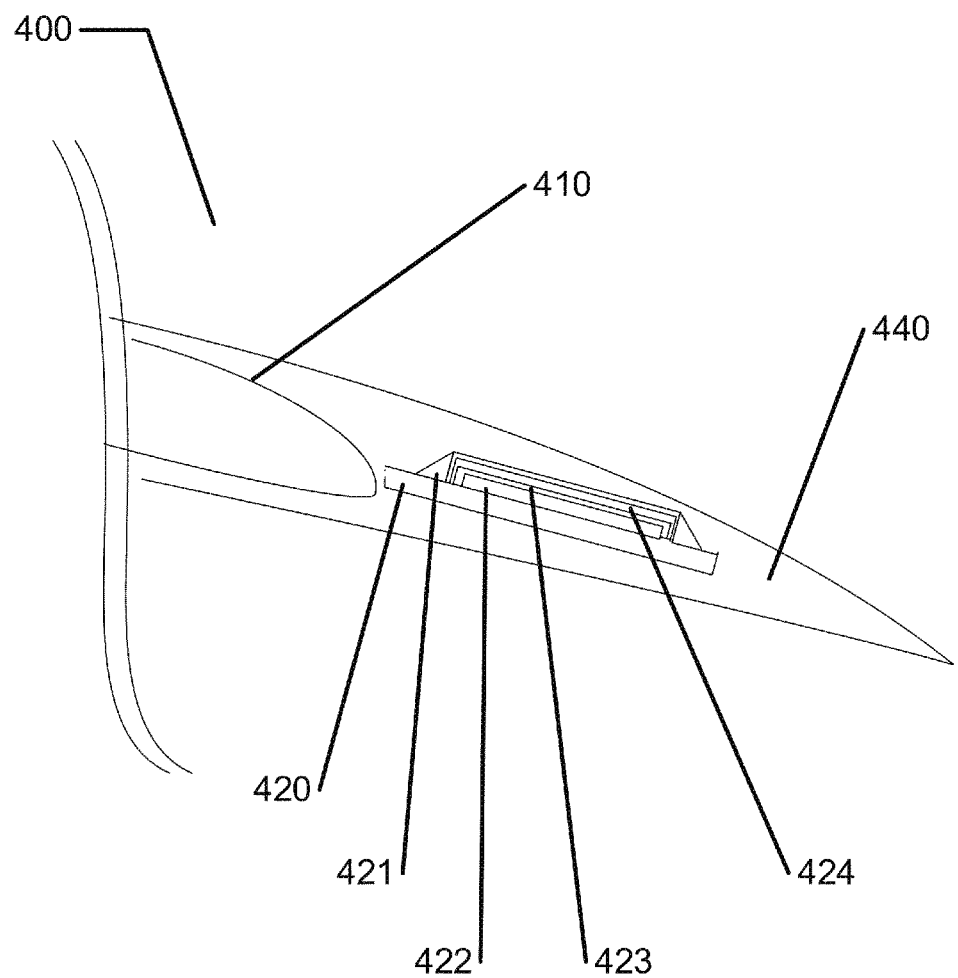
FIG. 4 illustrates an example of an energized ophthalmic lens in cross section.
Figure 5A:
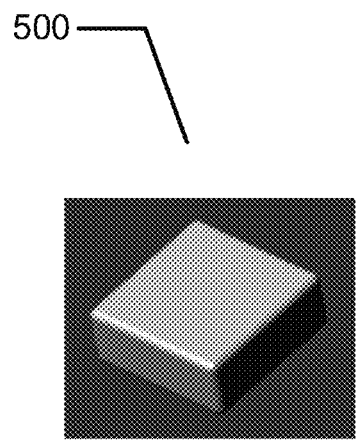
FIGS. 5A, 5B, 5C and 5D illustrate exemplary design shapes for energy sources.
Figure 5B:
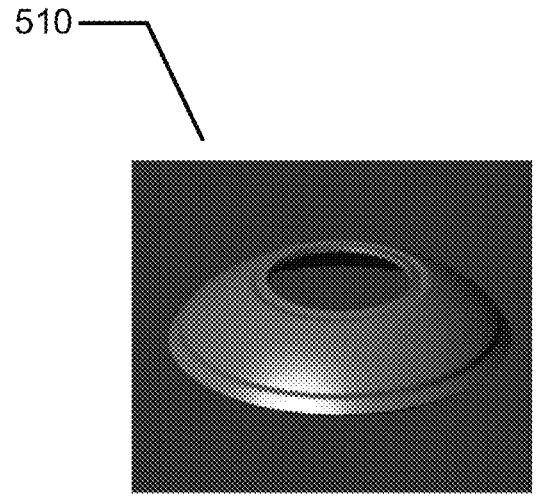
Figure 5C:
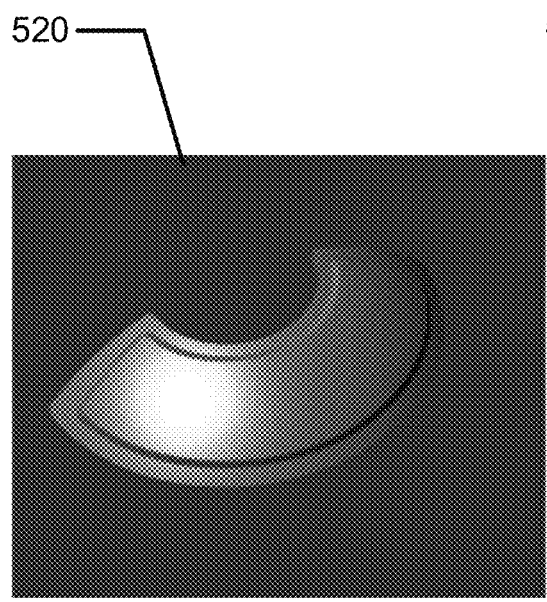
Figure 5D:
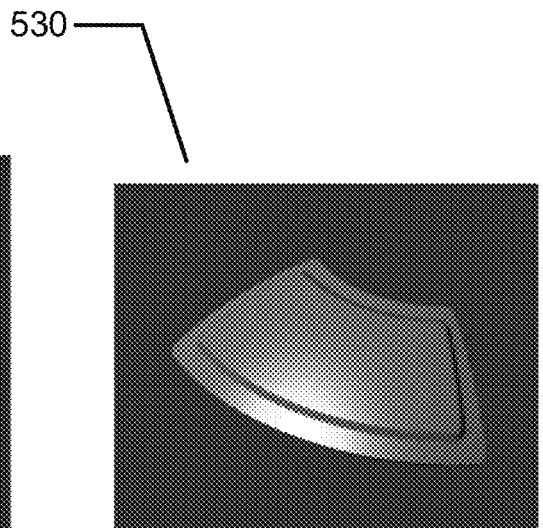

It may provide further exemplary descriptive purposes to consider how the example described in relation to FIG. 3 appears in a cross sectional representation. Such a cross section along the line in FIG. 3 shown as item 380 is depicted in FIG. 4 item 400. This depiction focuses on a cross section where the Energy Source device may be a thin film battery device. The cross section shows the general body of the ophthalmic lens, 440. Within that body 440 is the thin film battery with a substrate upon which it is built 420. Proceeding up from the substrate there may be a cathode layer 422 which may be surrounded by an electrolyte layer 423 which then may be coated by an anode layer 424. These layers may be surrounded by an encapsulating layer 421 that seals the battery layers from the external environment. In one exemplary embodiment the electronically controlled optic device may be shown as item 410. As mentioned above these descriptions are made in a non-limiting sense and many alternative embodiments of an energized and functional ophthalmic lenses may be apparent to those skilled in the art.

In some embodiments there may be manners of affecting the ophthalmic lens' appearance. Aesthetics of the thin film microbattery surface may be altered in various manners which demonstrate a particular appearance when embedded in the electroactive contact lens or shaped hydrogel article. In some embodiments the thin film microbattery may be produced with aesthetically pleasing patterned and/or colored packaging materials which serves to either give a muted appearance of the thin film microbattery or alternatively provide iris-like colored patterns, solid and/or mixed color patterns, reflective designs, iridescent designs, metallic designs, or potentially any other artistic design or pattern. In other embodiments, the thin film battery may be partially obscured by other components within the lens, for example a photovoltaic chip mounted to the battery anterior surface, or alternatively placement of the battery behind all or a portion of a flexible circuit. In further embodiments, the thin film battery may be strategically located such that either the upper or lower eyelid partially or wholly obscures the visibility of the battery. It may be apparent to one skilled in the art that there are numerous embodiments relating to appearance of an energized ophthalmic device and the methods to define them.

There may be numerous embodiments relating to the method of forming an energized ophthalmic device of the various types that have been described. In one set of embodiments, the inventive art herein may include assembling subcomponents of a particular energized ophthalmic lens embodiment in separate steps. The "off-line" assembly of advantageously shaped thin film microbatteries, flexible circuits, interconnects, microelectronic components, and/or other electroactive components in conjunction with a biocompatible, inert, conformal coating to provide an all-inclusive, embeddable singular package that can be incorporated into known cast molding contact lens manufacturing processes. Flexible circuits may include those fabricated from copper clad polyimide film or other similar substrates.

Conformal coatings may include, but are not limited to, parylene (grades N, C, D, HT, and any combinations thereof), poly(p-xylylene), dielectric coatings, silicone conformal coatings, polyurethane conformal coatings, acrylic conformal coatings, rigid gas permeable polymers, or any other advantageous biocompatible coatings.

Some embodiments of the present invention include methods that are directed toward the geometric design of thin film microbatteries in geometries amenable to the embedment within and/or encapsulation by ophthalmic lens materials. Other embodiments include methods for incorporating thin film microbatteries in various materials such as, but not limited to, hydrogels, silicone hydrogels, rigid gas-permeable "RGP" contact lens materials, silicones, thermoplastic polymers, thermoplastic elastomers, thermosetting polymers, conformal dielectric/insulating coatings, and hermetic barrier coatings.

Still other embodiments involve methods for the strategic placement of an Energy Source within an ophthalmic lens geometry. Specifically, in some embodiments the Energy Source may be an opaque article. Since the Energy Source may not obstruct the transmission of light through the ophthalmic lens, methods of design in some embodiments may ensure that the central 5-8 mm of the contact lens may not be obstructed by any opaque portions of the Energy Source. It may be apparent to one skilled in the art that there may be many different embodiments relating to the design of various Energy Sources to interact favorably with the optically relevant portions of the ophthalmic lens.

In some embodiments the mass and density of the Energy Source may facilitate designs such that said Energy Source may also function either alone or in conjunction with other lens stabilization zones designed into the body of the ophthalmic lens to rotationally stabilize the lens while on eye. Such embodiments are advantageous for a number of applications including, but not limited to, correction of astigmatism, improved on-eye comfort, or consistent/controlled location of other components within the energized ophthalmic lens.

In additional embodiments, the Energy Source may be placed a certain distance from the outer edge of the contact lens to enable advantageous design of the contact lens edge profile in order to provide good comfort while minimizing occurrence of adverse events. Examples of such adverse events to be avoided may include superior epithelial arcuate lesions or giant papillary conjunctivitis.

By way of non-limiting example in some embodiments, a cathode, electrolyte and anode features of embedded electrochemical cells may be formed by printed appropriate inks in shapes to define such cathode, electrolyte, and anode regions. It may be apparent that batteries thus formed include both single use cells, based for example on manganese oxide and zinc chemistries, and rechargeable thin batteries based on lithium chemistry similar to the above mentioned thin film battery chemistry. It may be apparent to one skilled in the arts that a variety of different embodiments of the various features and methods of forming energized ophthalmic lenses may involve the use of printing techniques.

There may be numerous embodiments relating to apparatus that may be used to form energized ophthalmic lens embodiments with the various methods that have been discussed. A fundamental step in the processing may relate to supporting the various components comprising an ophthalmic lens Energy Source while the body of the ophthalmic lens is molded around these components. In some embodiments the Energy Source may affixed to holding points in a lens mold. The holding points may be affixed with polymerized material of the same type that will be formed into the lens body. It may be apparent to one skilled in the art, that numerous manners of supporting the various Energy Sources before they are encapsulated into the lens body comprise embodiments within the scope of this invention.

Figure 7:
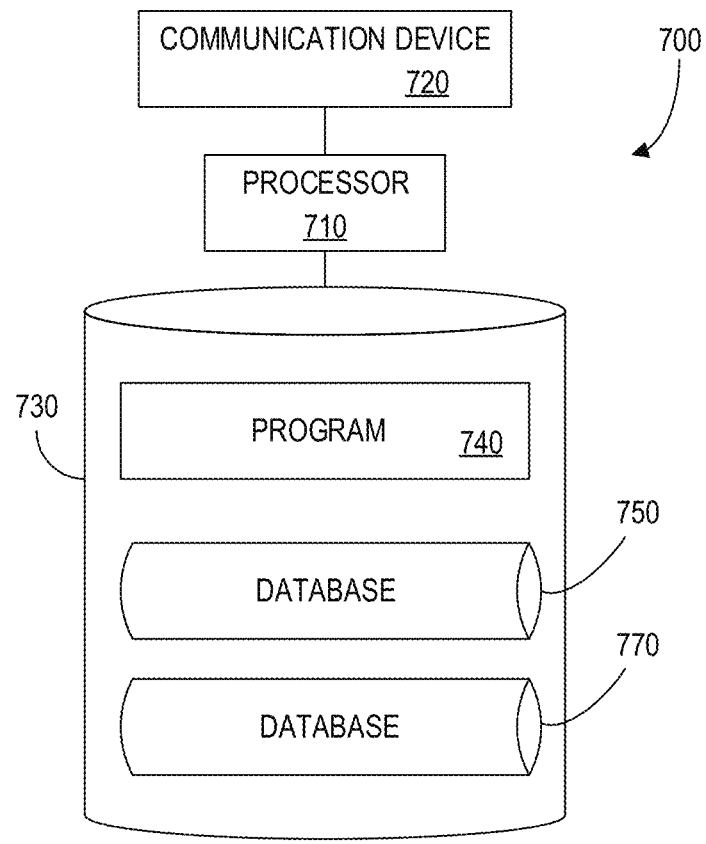
FIG. 7 illustrates a processor that may be suited to implement some aspects of the present invention.

Referring now to FIG. 7, a controller 700 that may be used in some embodiments of the present invention is illustrated. The controller 700 includes a processor 710, which may include one or more processor components coupled to a communication device 720. In some embodiments, a controller 700 can be used to transmit energy to the energy receptor placed in the ophthalmic lens.

The controller can include a one or more processors, coupled to a communication device configured to communicate energy via a communication channel. The communication device may be used to electronically control one or more of: the transfer of energy to the ophthalmic lens receptor and the transfer of digital data to and from an ophthalmic lens.

The communication device 720 may be used to communicate, for example, with one or more controller apparatus or manufacturing equipment components, such as for example ink jet printing apparatus for ink jetting conductive material or depositing a binder layer; and a pad printing device for depositing one or more binder layers.

The processor 710 is also in communication with a storage device 730. The storage device 730 may comprise any appropriate information storage device, including combinations of magnetic storage devices (e.g., magnetic tape and hard disk drives), optical storage devices, and/or semiconductor memory devices such as Random Access Memory (RAM) devices and Read Only Memory (ROM) devices.

The storage device 730 can store a program 740 for controlling the processor 710. The processor 710 performs instructions of the program 740, and thereby operates in accordance with the present invention. For example, the processor 710 may receive information descriptive of energy receptor placement, processing device placement, and the like. The storage device 730 can also store ophthalmic related data in one or more databases 750,770. The database may include customized energy receptor designs, metrology data, and specific control sequences for ink jetting conductive material to form an energy receptor.

In some embodiments, an ophthalmic lens with a component, such as processor device can be matched with an Energizing Source incorporated into an ophthalmic lens and used to perform logical functions or otherwise process data within the ophthalmic lens.

Energized Ophthalmic Lens Including Stacked Integrated Components

Following from the art described herein; in some embodiments, an energized ophthalmic lens may include components which have been integrated by stacking individual layers containing various components and component types into a novel device for incorporation into an ophthalmic lens. A basic architecture, similar to that described in FIGS. 3 and 4 provides an exemplary design to illustrate the art.

Figure 8:
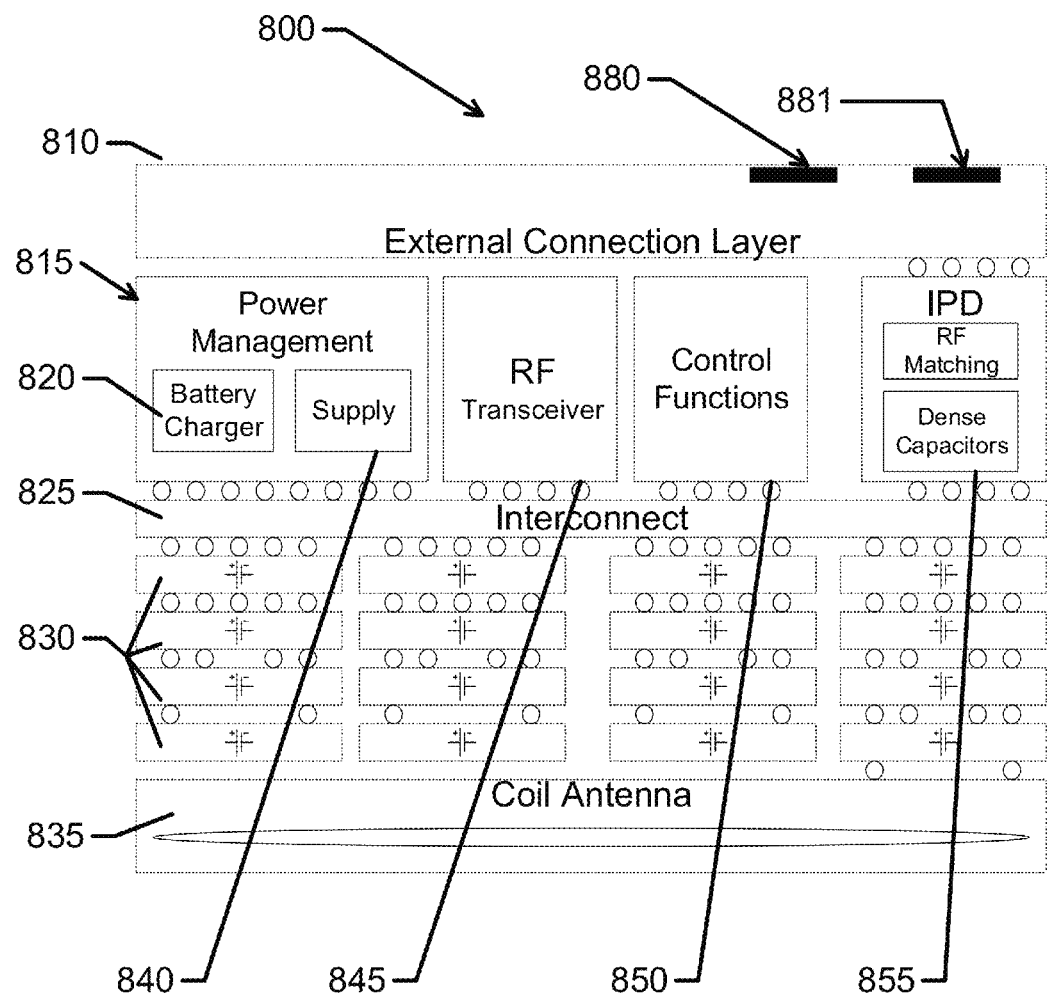
FIG. 8 illustrates a cross section of a stacked integrated component device with energization that may be used in some exemplary embodiments of Energized Ophthalmic Lenses.

Proceeding to FIG. 8, a cross sectional block diagram of a stacked integrated component for inclusion into an energized ophthalmic lens is depicted. The exemplary device may have eight layers as is shown. There may be different functions of the layers; for example the top layer, item 810, may function as an interconnection layer between the device and components external to the device through connection pads 880 and 881. A layer underneath the top layer, which may be seen as item 815, may function as a device layer, where numerous device functions may be incorporated. Proceeding down the stack of layers, item 825 may define in some embodiments an interconnection layer which routes power and signals amongst the various layers and the various devices within the layers. Continuing further, there may be numerous layers of discrete battery elements as shown as the four layers of item 830. In this exemplary embodiment, the bottom substrate layer may support the layers above it as well as provide the function of an antenna for wireless communication to the stacked integrated component.

As may be apparent to one skilled in the art, the example of item 800 may include the functional elements to control an active focus element within the ophthalmic lens. Proceeding to FIG. 9, for example, the incorporation of the stacked device may be seen into the energized ophthalmic lens, item 900. In some embodiments, the lens may be formed of a hydrogel lens body, depicted as item 930. Within the ophthalmic lens body may be located an electro active lens element, item 920 which may respond by altering the focal power of the ophthalmic lens under application of electrical signals to the element. Within this example, the stacked integrated component may be seen as item 910 with some of the device exposed in a cross sectional view. From this description, it will be apparent to a person of the ordinary skilled in the art that may be numerous manners to form an energized ophthalmic lens with stacked integrated components and there may be numerous functions that this type of device may perform.

Figure 9:
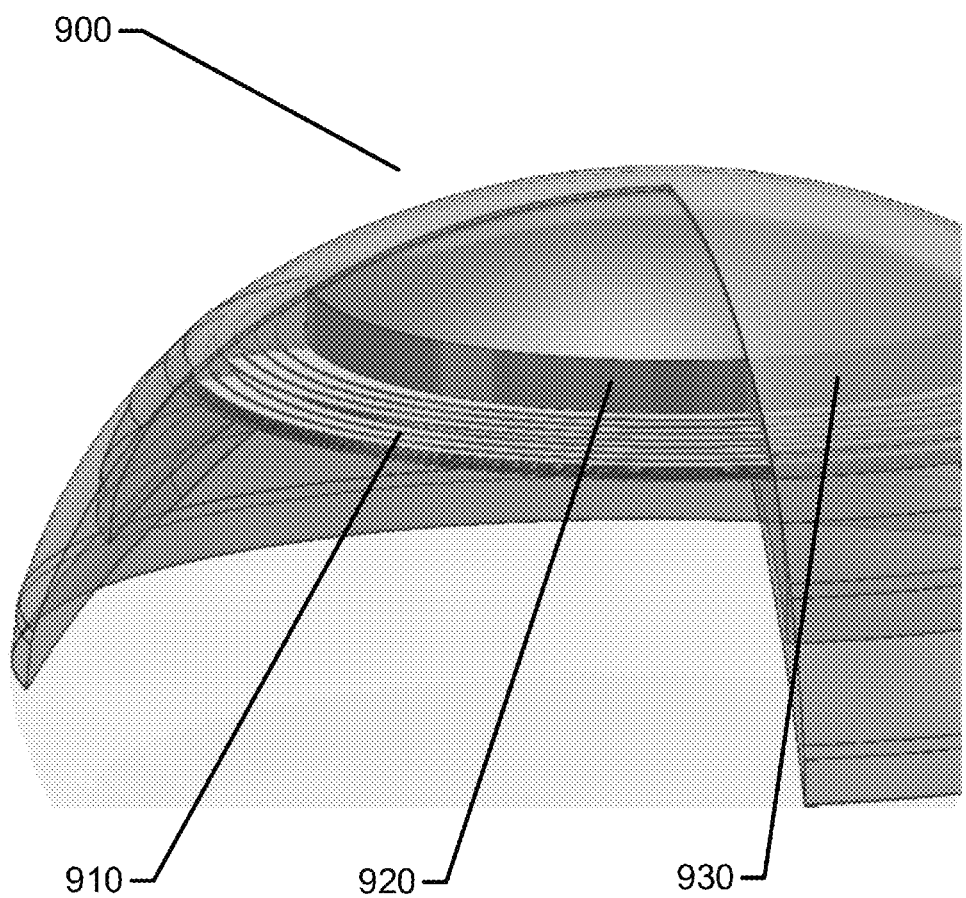
FIG. 9 illustrates a Stacked Integrated Component device as an exemplary embodiment for Energized Ophthalmic Lenses

Returning to FIG. 8, item 800, with the exemplary structure of item 900 of FIG. 9 in mind, the stacked integrated device may interact with its environment in at least the following manners. In a first example, the electroactive lens element may be connected to the stacked integrated component device by way of a set of wires bonded to the interface pads, 880, and 881, of the stacked device. In some embodiments, the application of a DC voltage signal between these two connections may cause the electroactive lens to change the shape of an internal lens meniscus interface and therefore can change the focusing power of the device to light incident on the front surface of the lens which exits to a users eye when worn in a standard manner that ophthalmic lenses may be worn.

To generate the exemplary DC signal to the output locations 880 and 881, the stacked integrated component device may have received a wireless activation signal upon its antenna, for example, in a layer 835. This electromagnetic signal may be transmitted along a carrier wave that can have a particular frequency range that matches a combination of the design of antenna 835 and electrical filtering devices including various passive inductors, capacitors and resistors of an integrated passive device, item 855, and in some embodiments active electrical amplification devices that may be present for example in item 845, an RF Transceiver component. It may be apparent to one skilled in the art that many different types of electrical signals may be applied to the external connections by the stacked device and numerous activation signals may be detected by the components in the stacked integrated component device to cause it to achieve a particular state of operation.

The received RF signal may be passed, in some examples, from the input receiving and filtering stages into the RF Transceiver, item 845. This component may include many examples of RF transceiver circuitry know in the state of the art to perform the function of extracting the signal from the RF carrier wave. This signal in some embodiments may comprise a digital based signal; while in other embodiments may be an analog signal. It may be based on amplitude modulation, frequency modulation or other signal encoding manners. The transceiver may further process the signal and provide a digital output to other components within the stacked integrated component device. There may be numerous manners to encode and transmit a signal to the energized lens and then for components in a stacked integrated component device to decode those signals for use in controlling components of the exemplary device.

In order for the energized ophthalmic lens to receive signals, process them and then apply the signals to an external device, an energized ophthalmic lens may need to have processing of internal control functions by various devices. In the example of item 800, an electronic device may exist as a control function processor, item 850, which receives signals and power through the interconnect layer 825 and transmits signals out along this layer as well. In some embodiments, the electroactive lens may be controlled to assume one of two optical powers. Some of the control functions in these type of embodiments may include determining the default state of the signal to the electroactive lens on activation, decoding the content of a signal transmitted to the lens to determine whether it is correctly associated with a control signal for itself, determining the content of any signal transmission and processing that content to determine the desired output state of the electroactive lens as well as numerous other control functions. As can be observed in the example of item 800 FIG. 8, there may be numerous paths within and through various stacked layers that can be used for power and signal routing.

An integral function of an energized ophthalmic lens may come from the manner that it is energized. Continuing with FIG. 8, items 820, 830, 835, 840 and 855 may all relate to the energization of the ophthalmic lens. A fundamental aspect may be illustrated by the components that make up item 830. In some embodiments, individual battery components may be combined in various layers to form the basic energy storage function of the stacked integrated component device. The power from these battery elements may be combined by the interconnections that are used between them, or alternatively each element may have a separate connection of its own. It may be apparent that various combinations of the battery elements comprise art within the scope of this invention. The connections of the battery elements or combinations of elements may be routed through the interconnect layer, 825, to the power management component in layer 815. In some embodiments, this component may take the various raw battery outputs of voltage and current capabilities and process them in various ways to obtain one or more power supply outputs that may be provided to the other various components in the integrated stacked component device.

In some embodiments, passive devices in element 855 may be employed in the energization of the device. Capacitors may be charged by the power management device, for example. In some examples, these capacitors may perform an important role in buffering quick or significant changes in the amount of current that the stacked integrated component device draws as a whole. In other cases, these capacitors may be employed in circuits which step up the voltage from battery voltages to higher voltages. Still further uses of passive devices in item 855 may relate to filtering of power supplies, to "clean" them of signal noise that in some cases may be present. There may be numerous roles that the passive devices of item 855 may perform in a stacked integrated component device.

In some embodiments, the battery elements depicted as item 830 may be single use or non rechargeable battery elements. Other embodiments, however may utilize battery elements that may be charged. In these examples, there can be components of the energization system that relate to recharging the batteries. An external charging signal may be wirelessly transmitted to an antenna placed into layer 835. This antenna may be a separate dedicated antenna for the purposes comprising receiving energy to charge battery elements. In other embodiments, a single antenna may receive multiple types of signals including those relating to providing energy for recharging battery elements. The energy from the antenna may be routed through the stacked integrated component device, and in some examples may first go to the power management devices. Within these devices, a battery charging function may be represented as item 820. The input power may be received and then modified into an appropriate voltage and current for charging some or all of the battery elements of item 830.

In some embodiments, the recharging may occur while the rest of the device functions are dormant. Still other embodiments may allow for simultaneous charging of battery elements while other functions are performed which draw energy from some of the battery elements.

Figure 10:
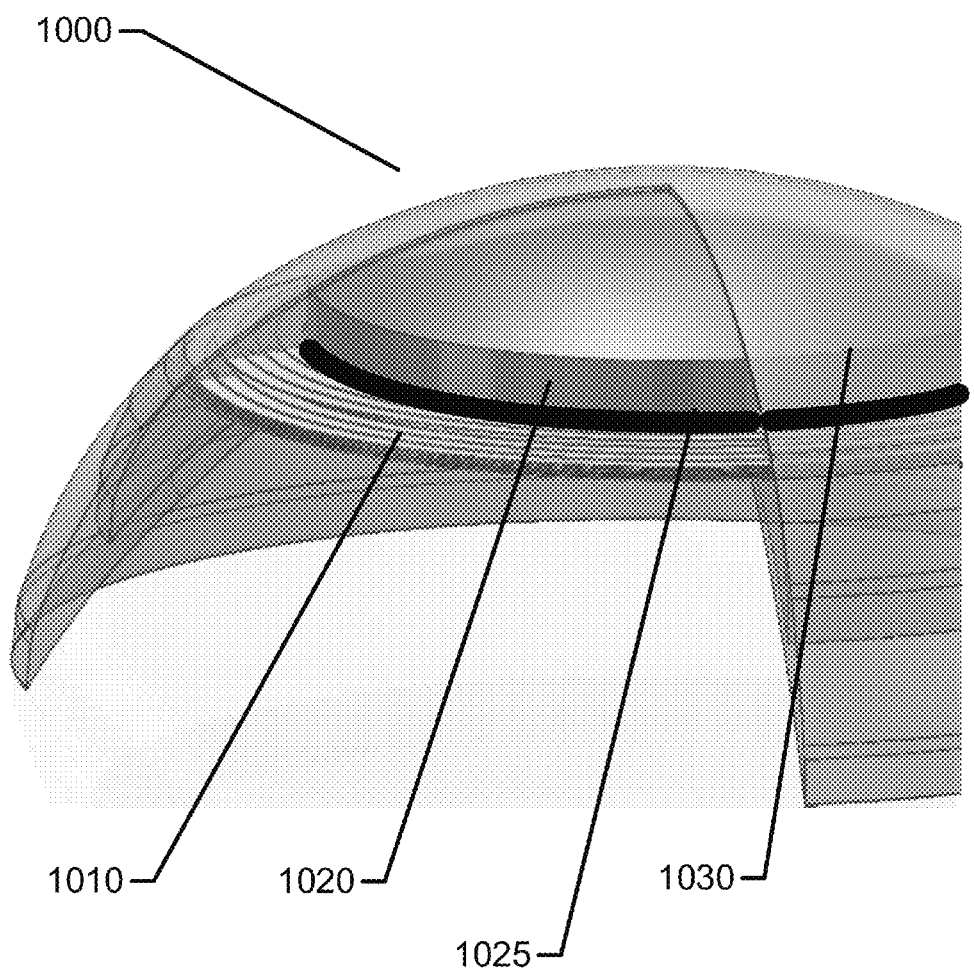
FIG. 10 illustrates an alternative Stacked Integrated Component Device with a Wire based energization source for Energized Ophthalmic Lenses

The descriptions that have been made herein have focused on a stacked integrated component device, where the battery elements are depicted as item 830 within the stack itself The similar diversity of function of a battery element may also derive when the battery is not a part of the stacked integrated component device, but rather is attached to in. Proceeding to FIG. 10, at item 1000, an example where the battery element is not part of the stacked integrated component device is provided. In a similar fashion to the energized ophthalmic lens embodiment of item 900, item 1000 may have a hydrogel ophthalmic lens body as shown as item 1030. It may also contain an electro active lens component depicted as item 1020. It also may have a stacked integrated component layer as shown by item 1010; however it may also have a wire battery element, item 1025, shaped to reside on the periphery of the electro active lens element 1020. This variations and examples are provided to put in context how a battery element connected externally to the stacked integrated component device may be formed; and in such a format, the function may in many ways can be equivalent to the description of battery elements that have been discussed herein. As well, as an example, it may be apparent that in fact numerous embodiments of different external battery components than a wire battery or the specific wire battery embodiment depicted may derive from the art within this invention.

It can be useful to describe some of the function that the exemplary devices depicted may perform that use the various component functions that have been described. An energized ophthalmic lens may be formed and acquire the shape and form as depicted in item 900. The stacked integrated component device may contain energization functions relating to rechargeable thin film battery elements. The device may be present in a charging environment where the battery elements are completely charged. A user of the device may install the ophthalmic lens upon their eye. The device may initially have a default condition that does not alter the focal conditions of light that intersects the lens and proceeds into the user's eye. The user may have a wireless transmitting device that when they activate, for example by pressing an electrical switch, sends an RF signal at an appropriate central band of frequencies for reception by the energized lens. The energized lens may receive the signal, and the signal being encoded upon the appropriate carrier frequency band pass the signal on to an RF transceiver component. The RF transceiver may upon receiving the signal, decode the signal and send a series of digital signals related to the input signal to a control function component in the stacked integrated component device. The control function component may process the digital signal, verify that the input signal is appropriate for further processing and then process the digital signal resulting in the information being decoded to cause the device to change the state of the optical element. Upon this processing, the control function component may send a signal back to the RF Transceiver which the RF transceiver may then processes into an output RF signal that may be routed to the antenna and then wirelessly to the control box that the user pressed a button on; where this transmission may in some cases verify the state change that is about to take place in the lens. At the same time the control function component may as well change the voltage that it applies across items 880 and 881 thereby changing the control signal to the electroactive lens. This change in control signal may electrically alter the focal properties of the electroactive lens, for example by causing an interfacial meniscus lens to distort the meniscus shape resulting in an increase in magnifying power of the electroactive lens. Images now incident upon the lens may be magnified as they pass through the lens. The user may now perceive that he is able to see an object in front of him with increased magnification. Although this example may be useful in describing how the stacked integrated components and the elements they are connected to inside an energized ophthalmic lens may function, it may be apparent that this is but one exemplary embodiment that may derive from the inventive concepts herein, and the example is not intended to limit the scope in any way.

The present invention, as described above and as further defined by the claims below, provides methods of processing ophthalmic lenses and apparatus for implementing such methods, as well as ophthalmic lenses formed thereby.

What is claimed is:

1. An energized ophthalmic lens device comprising:
   a lens with an optical zone and a non-optical zone comprising a silicon hydrogel material;
   an energy source embedded in the silicon hydrogel material in an area of the lens comprising the non-optical zone, wherein the energy source comprises a fuel cell;
   a stacked integrated component device at least partially embedded within the silicon hydrogel material in an area of the lens comprising the non-optical zone, the stacked integrated component device including one or more substrate layers stacked together into a single unit;
   one or more electrical current drawing components mounted to the one or more substrate layers of the stacked integrated component device; and
   an attachment area connecting the fuel cell to the one or more electrical current drawing components.

2. The device of claim 1 wherein the current drawing component is embedded in the non-optical zone.

3. The device of claim 1 wherein the fuel cell uses biologically available materials in the ophthalmic environment as a fuel source.

4. The device of claim 1 wherein the fuel cell uses a fuel source located within the energized ophthalmic lens device.

* * * * *